United States Patent [19]

Takeuchi et al.

[11] Patent Number: 5,614,331
[45] Date of Patent: Mar. 25, 1997

[54] MEDIUM AND HIGH DISCHARGE RATE COMBINATION BATTERY AND METHOD

[75] Inventors: Esther S. Takeuchi, East Amherst; Karen M. Walsh, Marilla, both of N.Y.

[73] Assignee: Wilson Greatbatch Ltd., Clarence, N.Y.

[21] Appl. No.: 577,260

[22] Filed: Dec. 22, 1995

[51] Int. Cl.⁶ .................................................. H01M 2/20
[52] U.S. Cl. .............................. 429/9; 429/153; 429/162; 429/163; 429/164
[58] Field of Search ........................... 429/9, 218, 127, 429/149, 152, 153, 154, 156, 161, 162, 163, 164, 165

[56] References Cited

U.S. PATENT DOCUMENTS

3,239,380 3/1966 Berchielli .
5,162,164 11/1992 Dougherty et al. ................... 429/9
5,223,351 6/1993 Wruck ..................................... 429/9
5,549,984 8/1996 Dougherty ........................... 429/61
5,563,002 10/1996 Harshe .................................. 429/7

Primary Examiner—M. Nuzzolillo
Attorney, Agent, or Firm—Hodgson, Russ, Andrews, Woods & Goodyear LLP

[57] ABSTRACT

A combination battery comprising a medium rate cell portion intended to be discharged under a substantially constant drain and a high rate cell portion intended to be pulse discharged, is described. Both cell portions are housed in the same casing and activated with the same electrolyte. The respective cells are capable of both independent and simultaneous discharge.

49 Claims, 5 Drawing Sheets

MEDIUM AND HIGH DISCHARGE RATE COMBINATION BATTERY AND METHOD

BACKGROUND OF THE INVENTION

1. Field of the Invention

The present invention generally relates to the conversion of chemical energy to electrical energy, and more particularly to a combination battery having at least two separate and distinct electrochemical cells housed inside the same battery casing. The combination battery preferably comprises both a constant discharge rate cell and a pulse discharge rate cell.

The constant discharge rate cell of the present invention, referred to hereinafter as the medium rate cell, preferably includes an electrode assembly comprising a single cathode structure flanked on either side by an alkali anode. The pulse discharge rate cell of the present invention, referred to hereinafter as the high rate cell, preferably includes an electrode assembly comprising a single cathode and anode that are wound together in a "jellyroll" fashion. Suitable separators are provided to prevent short circuiting and both cell assemblies are housed within the same hermetically sealed, prismatic casing.

2. Prior Art

It is well known to construct multicell batteries with each cell comprising a similar electrode assembly. It is believed that the combination battery of the present invention represents a pioneering advancement wherein a medium rate, constant discharge cell and a high rate, pulse discharge cell are contained within the same prismatic housing.

SUMMARY OF THE INVENTION

Particular implantable medical devices require power sources capable of providing low level currents for the maintenance of electronic monitoring circuits as well as high level currents during device activation. The present invention offers the advantage of having both a medium rate, constant discharge or constant drain cell and a high rate, pulse discharge cell disposed within the same metallic, prismatic housing. The electrochemical couple used for both of the cells is, for example, an alkali metal/mixed metal oxide couple such as a lithium-silver vanadium oxide cell. However, both cell couples need not necessarily be identical. Combination batteries according to the present invention having alternate medium rate and high rate cathode materials can be constructed/designed to meet the drain rate and current discharge requirements of a particular application.

The medium rate, constant discharge cell of the present combination battery contains a single cathode structure such as a cathode plate flanked on either side by an alkali metal anode. The cathode material, which preferably comprises a mixed metal oxide or a carbon/graphite intercalation compound, suitable conductive additive(s) and a binder, is in a dry powder form and is pressed onto a conductive metal screen. The alkali metal anode is preferably a piece of lithium or lithium-alloy foil that is also pressed onto a conductive metal screen. A metallic lead connects the cathode to a feedthrough terminal pin in the battery header which is insulated from the battery case by a glass-to-metal seal. The anode can either be connected to the case resulting in a case-negative configuration or to another feedthrough pin also located in the header of the battery. The cathode is encapsulated in a separator to prevent short circuiting.

The high rate, pulse discharge cell of the present combination battery contains a single cathode and anode that are wound together in a jellyroll fashion resulting in a high surface area electrode assembly capable of delivering high current pulses. The cathode material, which preferably comprises a mixed metal oxide, suitable conductive additive(s) and a binder, is calendared to form a flexible sheet having the desired thickness. The flexible sheet is cut to size and pressed onto a highly conductive metal screen to form the cathode. The lithium or lithium-alloy foil anode is also applied to a conductive metal screen by pressing. A separator is disposed between the anode and cathode electrodes to prevent short circuiting. A metallic lead connects the cathode to a positive feedthrough pin insulated from the header of the battery by a glass-to-metal seal. The anode is connected to the cell casing with a metallic lead. The medium rate and high rate cells are both activated with the same electrolyte.

These and other aspects of the present invention will become more apparent to those skilled in the art by reference to the following description and to the appended drawings.

DETAILED DESCRIPTION OF THE PREFERRED EMBODIMENTS

Figure 1:
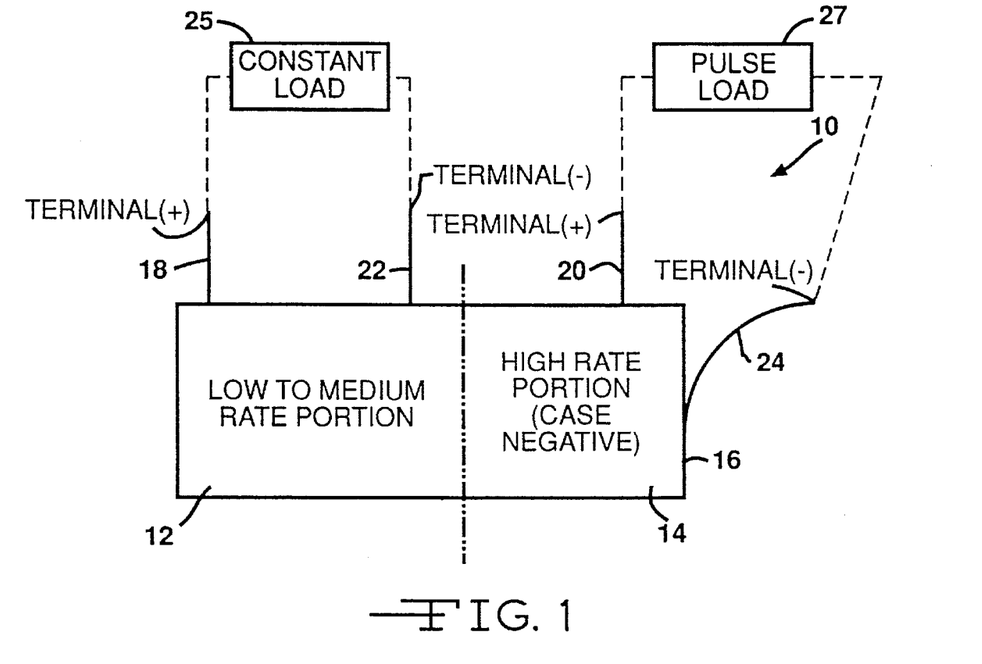
FIG. 1 is a schematic of one configuration of the combination battery of the present invention referred to as a Configuration "A" battery.
Figure 2:
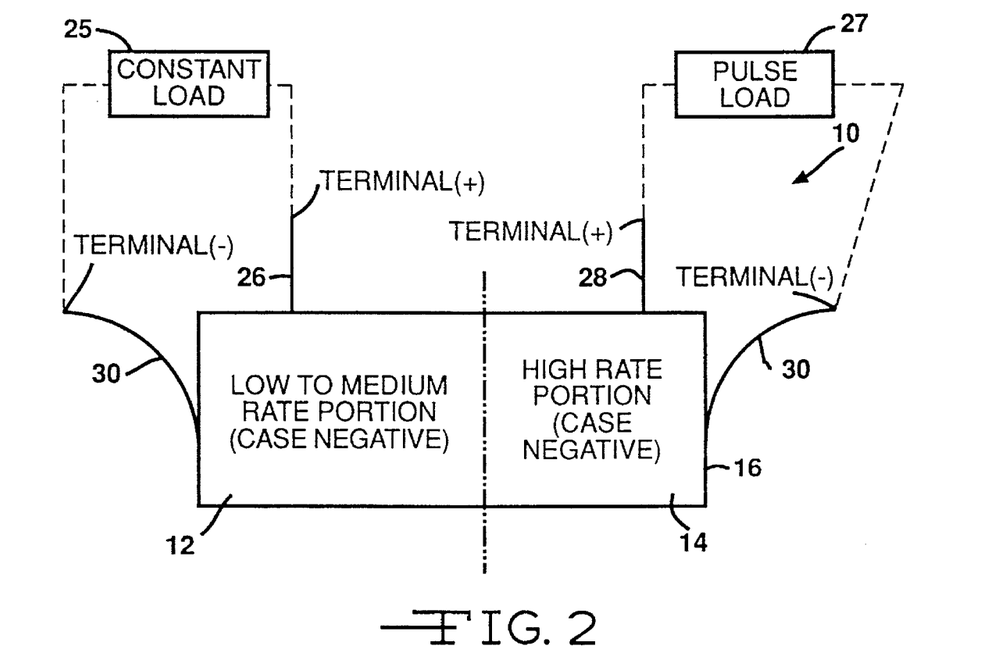
FIG. 2 is a schematic of another configuration of the combination battery of the present invention referred to as a configuration "B" battery.

Referring now to the drawings, FIGS. 1 and 2 show various schematic embodiments of the combination battery 10 constructed according to the present invention having both a medium rate, constant discharge cell 12 and a high rate, pulse discharge cell 14 hermetically sealed within a metallic, prismatic casing 16. Both electrode assemblies are insulated from one another and activated with the same electrolyte solution.

Two configurations are contemplated for the combination battery 10 of the present invention. As shown in FIG. 1, the first configuration has two positive terminals 18, 20 and two negative terminals 22, 24, i.e. one set each for the medium rate, constant drain cell and the high rate, pulse discharge cell. Two different loads are applied to this battery. A constant resistance load 25 is connected to the positive terminal 18 and the negative terminal 22 of the medium rate cell 12, and a constant current pulse "load" 27 is connected to the positive terminal 20 and the negative terminal 24 of the high rate cell 14. This combination battery is hereinafter referred to as the Configuration "A" battery.

As shown in FIG. 2, the second configuration comprises two positive terminals 26, 28 and a common negative terminal 30. In other words, the medium rate cell and the high rate cell have separate and distinct positive terminals and the same negative terminal, i.e., the prismatic casing 16. The two loads are applied to this battery such that the constant resistance load 25 is connected to the positive terminal 26 and the negative terminal 30, i.e., the casing 16, and the constant current pulse "load" 27 is connected to the position terminal 28 and the casing 16. This combination battery is referred to as the Configuration "B" battery. In either case, the housing 16 is vacuum filled with a nonaqueous electrolyte common to both the medium rate cell and the high rate cell. A device providing both a constant resistance load and a constant current pulse "load" is, for example, an implantable medical device such as a cardiac defibrillator.

More particularly, the anode electrode for each cell in both the Configuration A and B combination batteries of the present invention is selected from Group IA of the Periodic Table of Elements, including lithium, sodium, potassium, etc., and their alloys and intermetallic compounds including, for example Li—Si, Li—B and Li—Si—B alloys and intermetallic compounds. The preferred anode comprises lithium, and the more preferred anode comprises a lithium alloy, the preferred lithium alloy being lithium-aluminum with the aluminum comprising from between about 0% to about 50%, by weight, of the alloy. The greater the amount of aluminum present by weight in the alloy the lower the energy density of the cell.

The anode for the medium rate cell and the high rate cell is a thin metal sheet or foil of the anode metal, pressed or rolled on a metallic anode current collector, i.e., preferably comprising nickel, to form the respective anode components. In the combination battery of the present invention, for example, in the configuration B embodiment shown in FIG. 3, the respective anode components 32, 34 for both the medium and high rate cells 36, 38 each have an extended tab or lead 40, 42 of the same material as the anode current collector (not shown), i.e., preferably nickel, integrally formed therewith, such as by welding. In this configuration, the leads 40, 42 extending from the current collector of the anode components for both the medium rate cell 36 and the high rate cell 38 are contacted by a weld to the conductive metal battery casing 44 in a case-negative configuration for both cells. The battery casing 44 is preferably a prismatic housing that may comprise materials such as stainless steel, mild steel, nickel-plated mild steel, titanium or aluminum, but not limited thereto, so long as the metallic material is compatible for use with components of the cells.

The cathode electrode for both the medium rate and high rate cells of both battery Configurations A and B may comprise a metal element, a metal oxide, a mixed metal oxide, a metal sulfide or carbonaceous compounds, and combinations thereof. Suitable cathode active materials include silver vanadium oxide (SVO), copper vanadium oxide, copper silver vanadium oxide (CSVO), manganese dioxide, titanium disulfide, copper oxide, copper sulfide, iron sulfide, iron disulfide, carbon and fluorinated carbon, and mixtures thereof.

Preferably, the cathode active material comprises a mixed metal oxide formed by a chemical addition, reaction or otherwise intimate contact or by a thermal spray coating process of various metal sulfides, metal oxides or metal oxide/elemental metal combinations. The materials thereby produced contain metals and oxides of Groups IB, IIB, IIIB, IVB, VB, VIB, VIIB and VIII of the Periodic Table of Elements, which includes the noble metals and/or their oxide compounds.

By way of illustration, and in no way intended to be limiting, an exemplary cathode active material comprises silver vanadium oxide having the general formula $Ag_xV_2O_y$ in any one of its many phases, i.e., β-phase silver vanadium oxide having in the general formula x=0.35 and y=5.18, γ-phase silver vanadium oxide having in the general formula x=0.74 and y=5.37 and ε-phase silver vanadium oxide having in the general formula x=1.0 and y=5.5, and combination and mixtures of phases thereof.

In the case of the cathode electrode for the medium rate cell, the cathode active material in a dry powder form is pressed onto a conductive metal screen. Suitable materials for the cathode current collector include aluminum and titanium preferably comprising titanium. Preferably, the cathode active material is pressed onto the current collector screen with the aid of a suitable binder material such as a fluoro-resin powder, preferably polytetrafluoroethylene (PTFE) powder, and at least one material having electronic conductive characteristics such as graphite powder, acetylene black powder and carbon black powder. In some cases, no binder material or electronic conductor material is required to provide a similarly suitable cathode body. In some cases, the cathode electrode for the medium rate cell may also be prepared by rolling, spreading or pressing a mixture of the materials mentioned above onto a suitable current collector.

Figure 3:
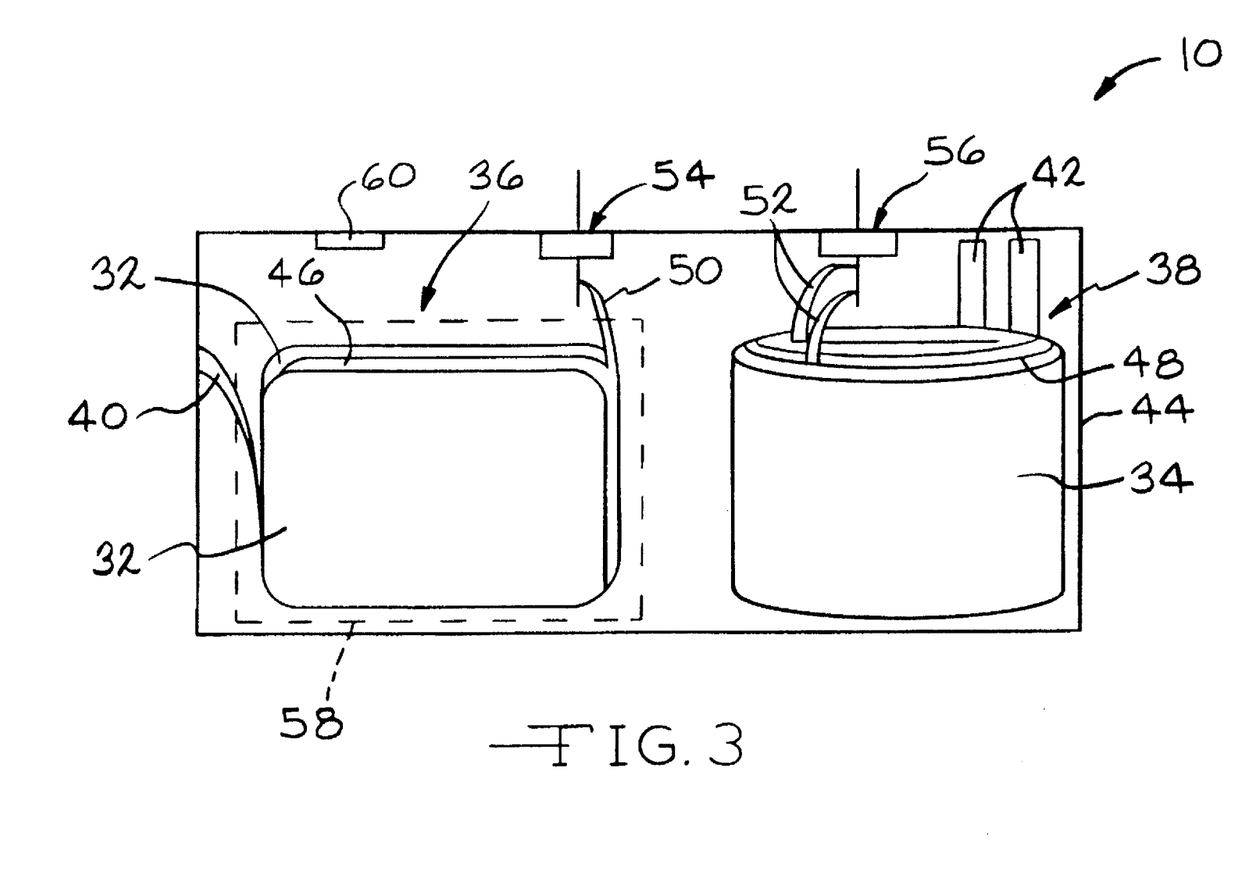
FIG. 3 is an elevational view, partly in schematic, of the Configuration B combination battery of the present invention shown in FIG. 2.

As shown with respect to the Configuration B combination battery of FIG. 3, the cathode electrode 46 for the medium rate cell 36, prepared as described above, is preferably in the form of one or more structures such as one or more cathode plates 46 operatively associated with at least one or more anode structures such as anode plate 32 of the previously described anode material. Preferably, at least one cathode electrode is flanked on either side by oppositely positioned anode electrodes, prepared as described above. While not shown in the drawings, the medium rate cell for the Configuration A combination battery of the present invention preferably has a similar construction.

As shown in FIG. 3, the high rate cell 38 of the Configuration B combination battery preferably has the cathode electrode 48 in the form of a strip wound with a corresponding strip of anode material in a structure similar to a "jellyroll". For that purpose, the cathode electrode 48 is in the form of a free-standing sheet of cathode material that has been calendared from a paste including binder and conductive additives, dried and cut to shape. The shaped cathode plate is then pressed onto at least one side and preferably both sides of a current collector screen of a suitable material such as aluminum or titanium with aluminum being preferred. A process for making cathode components useful in the high rate cell of the present combination battery is described in U.S. Pat. No. 5,435,874 to Takeuchi et al., which is assigned to the assignee of the present invention and incorporated herein by reference. While not shown, the Configuration A high rate cell preferably has a similar jellyroll structure.

As shown in FIG. 3, the lead 50 for the cathode electrodes 46 of the medium rate cell 36 and the leads 52 for the cathode electrode 48 of the high rate cell in the Configuration B battery are insulated from the casing 44 such as by respective glass-to-metal seal/terminal pin feedthroughs 54, 56. The glass used is of a corrosion resistant type having from between about 0% to about 50% by weight silicon such as CABAL 12, TA 23, FUSITE 425 or FUSITE 435. The positive terminal pin feedthroughs preferably comprise molybdenum although titanium, aluminum, nickel alloy, or stainless steel can also be used. The Configuration A battery likewise preferably has similar glass-to-metal seal/terminal pin feedthroughs for the cathode electrodes of both the medium rate and high rate cells and additionally for the anode electrode of the medium rate cell.

The cathode electrodes 46, 48 and the anode electrodes 32, 34 for both the medium rate and high rate cells are preferably sealed in their own separator envelopes (not shown in FIG. 3 for clarity) to prevent direct physical contact between the operatively associated anode electrodes and the cathode electrodes. In the case of the medium rate cell 36, an insulative bag 58 (shown in dashed lines in FIG. 3) is provided to surround the operatively associated cathode electrode 46 and anode electrode 32 to prevent direct contact between the medium rate and high rate cells. The insulative bag 58 is of a similar material as the separators. Similar separator structures and an insulative bag exist for the medium rate and high rate cells of the Configuration A combination battery.

In either case, the separator is of electrically insulative material to prevent an internal electrical short circuit between the electrodes, and the separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the respective cells. Illustrative separator materials include fabrics woven from fluoropolymeric fibers including polyvinylidine fluoride, polyethylenetetrafluoroethylene, and polyethylenechlorotrifluoroethylene laminated with a fluoropolymeric microporous film, non-woven glass, polypropylene, polyethylene, glass fiber material, ceramics, polytetrafluoroethylene membrane commercially available under the designations ZITEX (Chemplast Inc.), polypropylene membrane, commercially available under the designation CELGARD (Celanese Plastic Company, Inc.) and DEXIGLAS (C. H. Dexter, Div., Dexter Corp.)

The combination electrochemical battery of the present invention further includes a nonaqueous, ionically conductive electrolyte which serves as a medium for migration of ions between the anode and the cathode electrodes during the electrochemical reactions of both the medium rate and high rate cells. The electrochemical reaction at the electrodes involves conversion of ions in atomic or molecular forms which migrate from the anode to the cathode. Thus, nonaqueous electrolytes suitable for the present invention are substantially inert to the anode and cathode materials, and they exhibit those physical properties necessary for ionic transport namely, low viscosity, low surface tension and wettability.

A suitable electrolyte has an inorganic, ionically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. The inorganic, ionically conductive salt serves as the vehicle for migration of the anode ions to intercalate into the cathode active material, and has the general formula $MM'F_6$ wherein M is an alkali metal similar to the alkali metal comprising the anode and M' is an element selected from the group consisting of phosphorous, arsenic and antimony. Examples of salts yielding $M'F_6$ are: hexafluorophosphate ($PF_6$), hexafluoroarsenate ($AsF_6$) and hexafluoroantimonate ($SbF_6$). Alternatively, the corresponding sodium or potassium salts may be used.

Preferably the electrolyte comprises at least one ion-forming alkali metal salt of hexafluorophosphate, hexafluoroarsenate or hexafluoroantimonate dissolved in a suitable organic solvent wherein the ion-forming alkali metal is similar to the alkali metal comprising the anode of at least one of the medium and high rate cells of the present combination battery. Thus, in the case of an anode comprising lithium, the alkali metal salt comprises lithium hexafluorophosphate, lithium hexafluoroarsenate or lithium hexafluoroantimonate dissolved in a suitable solvent mixture. Other inorganic salts useful with the present invention include $LiBF_4$, $LiClO_4$ and $LiCF_3SO_3$, and mixtures thereof.

Low viscosity solvents include tetrahydrofuran (THF), methyl acetate (MA), diglyme, triglyme, tetraglyme, dimethyl carbonate (DMC), 1,2-dimethoxyethane (DME) and mixtures thereof, and high permittivity solvents include cyclic carbonates, cyclic esters and cyclic amides such as propylene carbonate (PC), ethylene carbonate (EC), acetonitrile, dimethyl sulfoxide, dimethyl formamide, dimethyl acetamide, γ-butyrolacetone (GBL) and N-methyl-pyrrolidinone (NMP) and mixtures thereof. In the present invention, the anode is lithium metal and the preferred electrolyte is 1.0M to 1.4M $LiAsF_6$ dissolved in an aprotic solvent mixture comprising a 50/50 mixture (by volume) of propylene carbonate (PC) and dimethoxyethane (DME).

The casing header comprises a metallic lid (not shown) having a sufficient number of openings to accommodate the glass-to-metal seal/terminal pin feedthroughs for the cathode electrodes for the medium and high rate cells and the anode electrode for the high rate cell in the Configuration A embodiment of the present combination battery and for the cathode electrodes for the medium and high rate cells in the case of the Configuration B embodiment. An additional opening is provided for electrolyte filling. The casing header comprises elements having compatibility with the other components of the electrochemical cells and is resistant to corrosion. The battery is thereafter filled with the electrolyte solution described hereinabove and hermetically sealed such as by close-welding a stainless steel plug over the fill hole 60 (FIG. 3), but not limited thereto.

The following examples describe the manner and process of a combination battery according to the present invention, and they set forth the best mode contemplated by the inventors of carrying out the invention, but they are not to be construed as limiting.

EXAMPLE I

Ten combination batteries were constructed according to the present invention having an external volume of approximately 10 cc and containing both a medium rate, constant drain cell and high rate, pulse discharge cell, as described above. Half of the batteries were configured with separate terminals as per Configuration A in FIG. 1 and half of the batteries were configured with a common negative terminal as per Configuration B in FIG. 2.

The high rate, pulse discharge cells of these ten batteries contained sheeted cathodes pressed to aluminum screen current collectors while the medium rate constant drain cells contained pressed powder cathodes associated with titanium screen current collectors. The cathode material incorporated into both cells of the batteries comprised a mixed metal oxide, specifically silver vanadium oxide, conductive carbon additives and a suitable binder. The high rate, pulse discharge cathodes were approximately 0.009" thick, 0.67" tall and 13.25" long. The average amount of cathode mix in the high rate cells of the batteries was 2.79 g which corresponds to an average theoretical capacity of 825 mAhrs. The medium rate, constant drain cathodes were approximately 0.179" thick, 0.679" tall and 0.843" long. The average amount of cathode mix in the medium rate cells of the batteries was 3.58 g which corresponds to an average theoretical capacity of 1059 mAhrs.

The high rate cell anodes comprised 99.9% LiAl alloy (0.1% Al) and were approximately 0.0045" thick, 0.62" tall and 14.25" long. The medium rate cell anodes comprised second pulses with 15 second rests between each pulse, every 30 minutes and discharging the medium rate cells under a constant resistive load of 500Ω to 1.4 V. The first regime included four of the thusly constructed batteries, two of each Configuration A and B, and called for the discharge of the high rate cells first, followed by the discharge of the medium rate cells. The second regime also included two batteries of each configuration, however, the order of discharge was reversed and in the third, only one Configuration A battery was used with both the medium rate cell and the high rate cell discharged simultaneously.

Table 1 shows the average capacity delivered to 2.0 V, 1.7 V and 1.5 V for both cells of each battery for each configuration and test regime. However, for Test Regime 3, only one Configuration A battery was discharged so the indicated capacities for that regime are not averages.

TABLE 1

| | | CAPACITY DELIVERED DURING DISCHARGE | | | | | |
|---|---|---|---|---|---|---|---|
| Test | | High Rate Portion Average mAhrs delivered to | | | Medium Rate Portion Average mAhrs delivered to | | |
| Regime* | Configuration | 2.0 V | 1.7 V | 1.5 V | 2.0 V | 1.7 V | 1.5 V |
| 1 | A | 539 | 644 | 697 | 828 | 933 | 966 |
| 1 | B | 567 | 678 | 729 | 942 | 1045 | 1083 |
| 2 | A | 524 | 630 | 680 | 948 | 1039 | 1075 |
| 2 | B | 538 | 638 | 683 | 901 | 1006 | 1053 |
| 3 | A | 350 | 588 | 655 | 716 | 800 | 855 |

*Test Regime 1 = High Rate Cell Portion Discharged First
Test Regime 2 = Medium Rate Cell Portion Discharged First
Test Regime 3 = High Rate and Medium Rate Cell Portions Discharged Simultaneously pure lithium foil and were approximately 0.055" thick, 0.649" tall and 0.813" long. The anodes for both cells of each battery were applied to a nickel screen current collector. An average of 0.356 g of lithium was incorporated into the high rate cells of the batteries and an average of 0.351 g of lithium was incorporated into the medium rate cells of the batteries. This corresponds to 1372 mAhrs and 1353 mAhrs of capacity, respectively.

Both the cathode and anode of each of the high rate cells were encapsulated with a 0.001" polypropylene separator and wound together in a flattened jellyroll configuration. The cathodes of each of the medium rate cells were encapsulated with a 0.0035" polypropylene film laminate separator and flanked on either side by the lithium anodes. Both cells, i.e., one of the medium rate, constant discharge cells and one of the high rate, pulse discharge cells were secured in a hermetically sealed prismatic case vacuum filled with an average of 4.29 g of 1M LiAsF$_6$ PC/DME (50:50). The active surface area of the high rate and medium rate cells was 114 cm$^2$ and 4.7 cm$^2$, respectively.

A constant resistive load of 7.5 kΩ was applied to the high rate cell of each of the ten batteries during an initial pre-discharge period which depleted this portion of the battery of approximately 1.1% of its theoretical capacity. The medium rate cell of each of the batteries were also pre-discharged with a constant resistive load of 7.5 k Ω, depleting the cells of <0.5% of their theoretical capacity. The high rate cells of the batteries were pre-discharged first, followed by the medium rate cells.

Following the initial pre-discharge, the batteries of this example were discharged by three different test regimes. All three regimes involved discharging the high rate cells to 1.4 V by applying a 2.0 Amp pulse train, consisting of four 10

Figure 4:
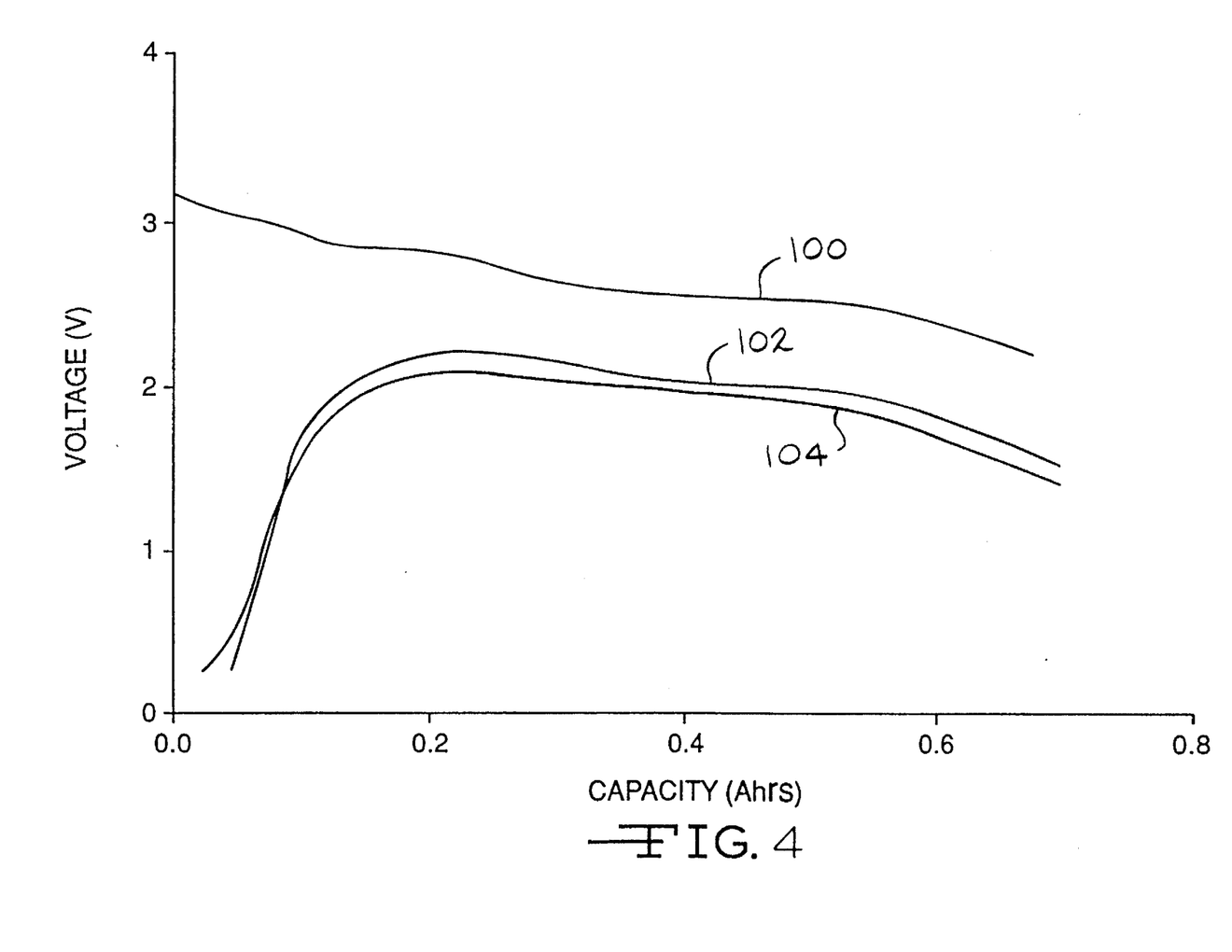
FIG. 4 is a graph showing the pulse discharge voltages versus amp hours for the high rate cell of a Configuration A combination battery of the present invention constructed as shown in FIG. 1 with both the medium rate cell and high rate cell discharged simultaneously.
Figure 5:
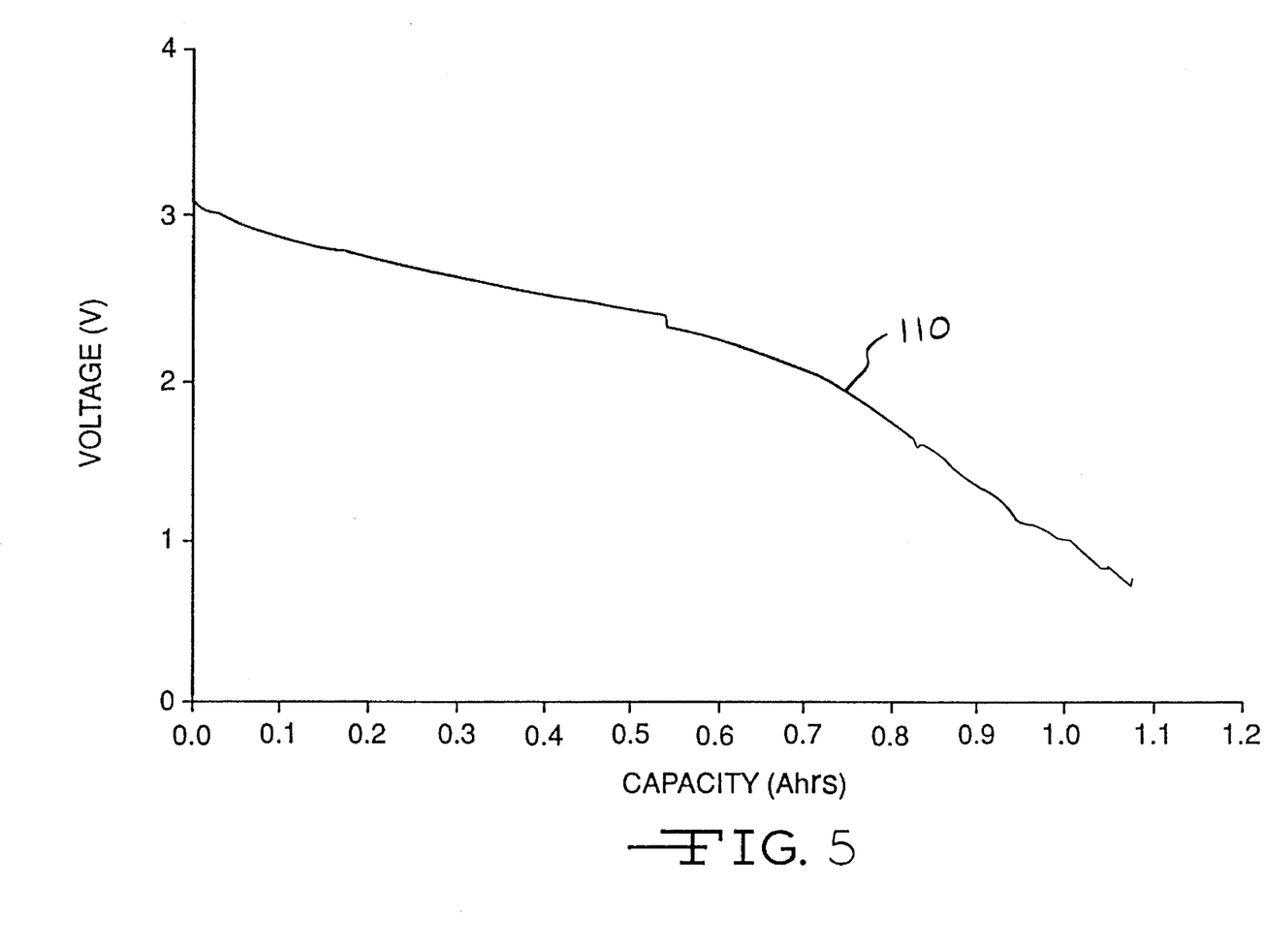
FIG. 5 is a graph showing the constant load discharge voltage versus amp hours for the medium rate cell of the Configuration A battery of the present invention discharged to construct the graph shown in FIG. 4 with both the medium rate cell and high rate cell discharged simultaneously.

FIGS. 4 and 5 are graphs constructed showing the average voltage versus delivered capacity for the battery in this example constructed according to Configuration A and discharged under the third test regime, i.e. the battery having separate terminals for the anode and cathode components of both the medium rate cell and the high rate cell in which both cells were discharged simultaneously. Specifically, FIG. 4 is a graph showing the pulse discharge voltages versus amp hours for the high rate cell wherein curve 100 was constructed from the open circuit voltage (OCV) of the high rate cell, curve 102 was constructed from the first pulse minima of the cell and curve 104 was constructed from the fourth pulse minima of the cell of the Configuration A battery. FIG. 5 is a graph showing the discharge voltage versus amp hours curve 110 for the medium rate, constant drain cell of the battery constructed according to Configuration A.

EXAMPLE II

Four cells were constructed with an external volume of approximately 10 cc and containing both a medium rate, constant drain cell and high rate, pulse discharge cell, as described above. All of the batteries were configured with a common negative terminal as per Configuration B shown in FIGS. 2 and 3.

The average amount of cathode mix in the high rate cells was 2.56 g which corresponds to an average theoretical capacity of 759 mAhrs. The average amount of cathode mix in the medium rate cells was 4.49 g which corresponds to an average theoretical capacity of 1329 mAhrs. An average of 0.278 g of lithium was incorporated into the high rate cells and an average of 0.377 g of lithium was incorporated into the medium rate cells. This corresponds to 1074 mAhrs and 1457 mAhrs of capacity, respectively. The batteries were vacuum filled with an average of 4.93 g of 1M LiAsF$_6$ PC/DME (50:50).

A constant resistive load of 7.5 k Ω was applied to the high rate cells of these batteries during an initial pre-discharge period which depleted this portion of the batteries of approximately 1.1% of their theoretical capacity. The medium rate cells were also pre-discharged with a constant resistive load of 1.5 k Ω, depleting these cells of approximately 1.2% of their theoretical capacity. A 2.0 amp pulse train consisting of four 10 second pulses with 15 second rest periods between each pulse was applied to the high rate cells of the batteries 24 hours after the pre-discharge period to verify the pulsing capabilities of the batteries.

Following the initial pre-discharge, the combination batteries of this example were tested to simulate their usage in a medical device. A 2.0 Amp pulse train, as described above, i.e. consisting of four 10 second pulses with 15 second rest periods between each pulse was applied to the high rate cells of the batteries every 60 days to simulate the periodic pulsing required, e.g., in a defibrillator. The medium rate cells of the batteries were placed under a constant resistance load of 2.67 k Ω to simulate the low level current drain required to maintain implantable medical device operation.

Figure 6:
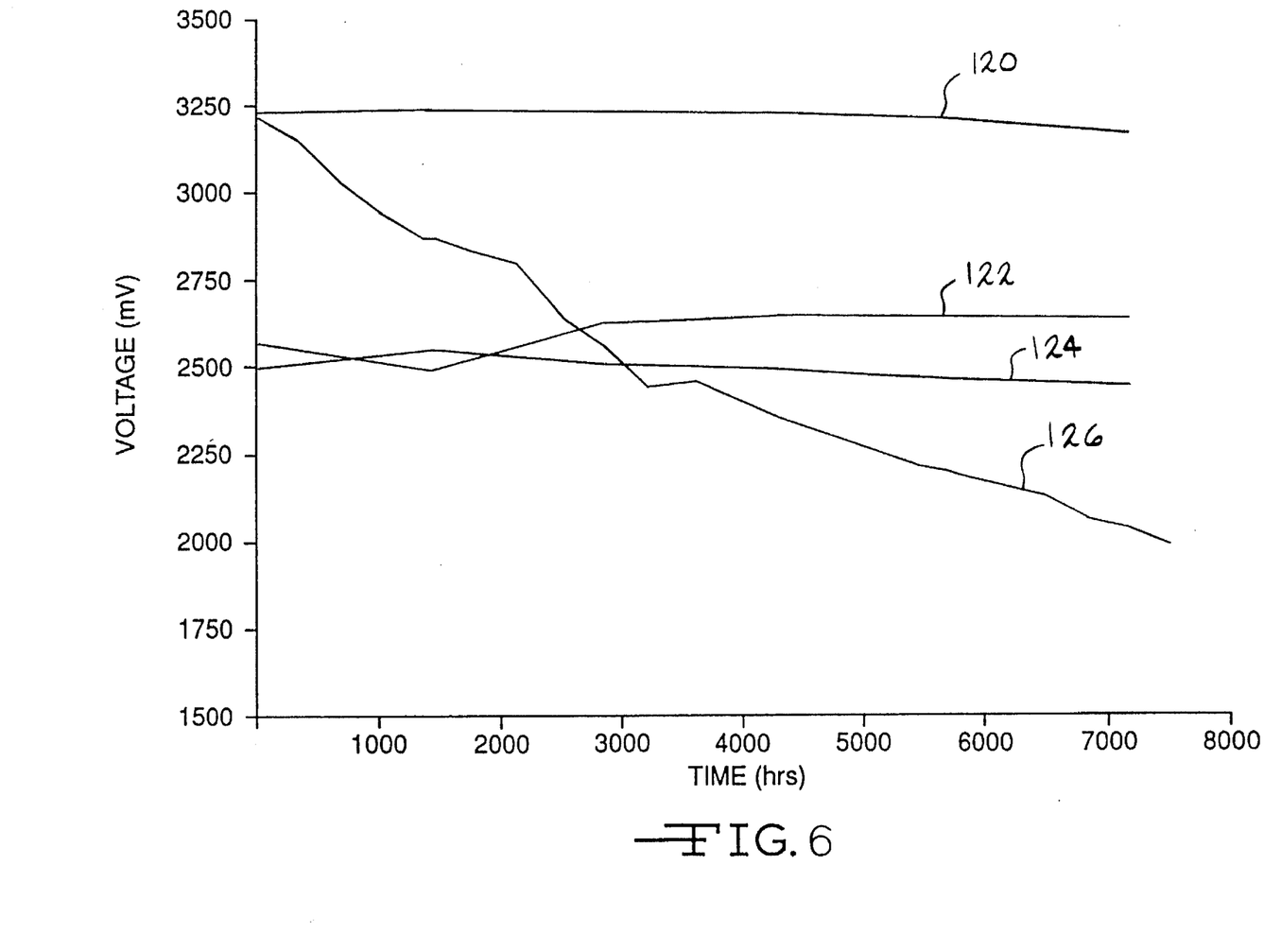
FIG. 6 is a graph showing the average discharge voltages for four batteries constructed according to the Configuration B combination of the present invention shown in FIG. 2 wherein the medium rate cell and the high discharge rate cell of each battery were discharged simultaneously under a long term test regime.

FIG. 6 is a graph showing the average discharge voltages for both the medium rate and high rate cells of the thusly discharged batteries. Specifically, curve 120 was constructed from the average open circuit voltage of the high rate cells of these batteries, curve 122 was constructed from the average of the first pulse minima of these cells and curve 124 was constructed from the average of the fourth pulse minima of these cells. The pulse trains applied to the high rate cells of the batteries are above the 2.0 V cut-off often required in defibrillator devices. Curve 126 was constructed from the average discharge curve of the medium rate cells of Example II and shows the characteristic voltage plateaus of the lithium/silver vanadium oxide couple.

It has been shown, in Table 1 and FIGS. 4 to 6, that the combination battery of the present invention, which incorporates both a medium rate cell and high rate cell in the same prismatic housing with a common electrolyte reservoir, meets the designated intent of the invention. In other words, the high and medium rate cells of the combination batteries constructed according to Configuration A and B discharged simultaneously in a manner required for certain implantable medical devices.

It is appreciated that various modifications to the inventive concepts described herein may be apparent to those skilled in the art without departing from the spirit and scope of the present invention defined by the hereinafter appended claims.

What is claimed is:

1. An electrochemical battery, comprising:
   a) a casing means;
   b) a first electrochemical cell housed within the casing means, the first cell comprising:
      i) a first anode means comprising alkali metal electrically associated with a first anode current collector;
      ii) means for connecting the first anode current collector to an external lead;
      iii) a first cathode means of cathode active material electrically associated with a first cathode current collector;
      iv) means for connecting the first cathode current collector to an external lead; and
      v) an electrolyte operatively associated with the first anode means and the first cathode means; and
   c) a second electrochemical cell housed within the casing means, the second cell comprising:
      i) a second anode means comprising alkali metal electrically associated with a second anode current collector;
      ii) means for connecting the second anode current collector to an external lead;
      iii) a second cathode means of cathode active material electrically associated with a second cathode current collector;
      iv) means for connecting the second cathode current collector to an external lead; and
      v) the electrolyte operatively associated with the second anode means and the second cathode means; and
   wherein the first cell is dischargeable independent of the second cell to provide separate and independent sources of electrical energy.

2. The electrochemical battery of claim 1 wherein the first cell is dischargeable under a substantially constant discharge rate and the second cell is dischargeable under a current pulse discharge application.

3. An electrochemical battery, comprising:
   a) a casing means of electrically conductive material;
   b) a first electrochemical cell housed within the casing means, the first cell comprising:
      i) a first anode means comprising alkali metal electrically associated with a first anode current collector;
      ii) a first cathode means of cathode active material electrically associated with a first cathode current collector; and
      iii) an electrolyte solution operatively associated with the first anode means and the first cathode means; and
   c) a second electrochemical cell housed within the casing means, the second cell comprising:
      i) a second anode means comprising alkali metal electrically associated with a second anode current collector;
      ii) a second cathode means of cathode active material electrically associated with a second cathode current collector; and
      iii) the electrolyte solution operatively associated with the second anode means and the second cathode means; and
   wherein the first cell is dischargeable independent of the second cell to provide separate and independent sources of electrical energy.

4. The electrochemical battery of claim 3 wherein the first cell is dischargeable under a substantially constant discharge rate and the second cell is dischargeable under a current pulse discharge application.

5. The electrochemical battery of claim 3 wherein the first and second anode current collectors are electrically connected to the casing means to provide a case-negative configuration for the first and second cells.

6. The electrochemical battery of claim 3 wherein either of the first and second anode current collectors is electrically connected to the casing means to provide a case-negative configuration for the corresponding first and second electrochemical cell and the other of the first and second anode current collectors is connected to an anode terminal means electronically insulated from the casing means.

7. The electrochemical battery of claim 6 wherein both the first and second cathode current collectors are electrically connected to respective cathode terminal means electrically insulated from the casing means.

8. The electrochemical battery of claim 3 wherein both the first and second anode current collectors are electrically connected to respective anode terminal means electrically insulated from the casing means.

9. The electrochemical battery of claim 8 wherein both the first and second cathode current collectors are electrically connected to respective cathode terminal means electrically insulated from the casing means.

10. The electrochemical battery of claim 3 wherein the anode is comprised of lithium.

11. The electrochemical battery of claim 3 wherein the anode comprises a lithium-aluminum alloy.

12. The electrochemical battery of claim 11 wherein aluminum comprises from between about 0% to about 50% by weight of the anode alloy.

13. The electrochemical battery of claim 3 wherein the electrolyte solution operatively associated with both the first and second electrochemical cells comprises an inorganic salt having the general formula $MM'F_6$ dissolved in a nonaqueous solvent, wherein M is an alkali metal similar to the alkali metal comprising at least one of the anode means and M' is an element selected from the group consisting of phosphorous, arsenic and antimony.

14. The electrochemical battery of claim 13 wherein the alkali metal of both the first and second anode means comprises lithium and the inorganic salt comprising the electrolyte solution is lithium hexafluorophosphate.

15. The electrochemical battery of claim 13 wherein the nonaqueous solvent comprises an organic solvent selected from the group consisting of tetrahydrofuran, propylene carbonate, methyl acetate, acetonitrile, dimethyl sulfoxide, dimethyl formamide, dimethyl acetamide, ethylene carbonate, diglyme, triglyme, tetraglyme, 1,2-dimethoxyethane and mixtures thereof.

16. The electrochemical battery of claim 13 wherein the nonaqueous solvent is an organic solvent that comprises propylene carbonate and dimethoxyethane.

17. The electrochemical battery of claim 16 wherein the propylene carbonate and dimethoxyethane are present in a ratio of about 1:1 by volume.

18. The electrochemical battery of claim 3 wherein the cathode active material of both the first and second cathode means is selected from the group consisting of silver vanadium oxide, copper silver vanadium oxide, manganese dioxide, cobalt oxide, nickel oxide, copper oxide, titanium disulfide, copper sulfide, iron sulfide, iron disulfide copper vanadium oxide, carbon and fluorinated carbon and mixtures thereof.

19. The electrochemical cell of claim 3 wherein at least one of the cathode means comprises a calendared mixed metal oxide.

20. The electrochemical battery of claim 3 wherein the cathode active material of both the first and second cathode means comprises a mixed metal oxide formed as a preparation product of one of the group consisting of a thermal treatment reaction, addition reaction, sol-gel formation, chemical vapor deposition and hydrothermal synthesis of vanadium oxide and a second metal.

21. The electrochemical battery of claim 3 wherein both the first and second cathode means comprise from between about 80 weight percent to about 99 weight percent of the cathode active material.

22. The electrochemical battery of claim 3 wherein at least one of the first and second cathode means further comprises binder material and conductive additives.

23. The electrochemical battery of claim 22 wherein the binder material is a fluoro-resin powder.

24. The electrochemical battery of claim 22 wherein the conductive additives are selected from the group consisting of carbon, graphite powder, acetylene black and mixtures thereof.

25. The electrochemical battery of claim 3 wherein the first and second cathode means comprise about 0 to 3 weight percent carbon, about 1 to 5 weight percent of a powder fluoro-resin and about 94 to 99 weight percent of the cathode active material.

26. The electrochemical battery of claim 3 wherein the cathode means of the second cell is formed of a cathode sheet having a thickness in the range of from between about 0.004 inches to about 0.020 inches associated with the anode means in a jellyroll configuration.

27. An electrochemical battery, comprising:

a) a casing means of electrically conductive material;

b) a first electrochemical cell housed within the casing means and dischargeable under a substantially constant discharge application, the first cell comprising:

i) a first anode means comprising alkali metal electrically associated with a first anode current collector;

a first cathode means of cathode active material selected from the group consisting of a metal, a metal oxide, a mixed metal oxide, a metal sulfide and a carbonaceous compound, and mixtures thereof, electrically associated with a first cathode current collector; and iii) an electrolyte solution operatively associated with the first anode means and the first cathode means; and c) a second electrochemical cell housed within the casing means and dischargeable under a current pulse discharge application, the second cell comprising:

i) a second anode means comprising alkali metal electrically associated with a second anode current collector;

ii) a second cathode means of cathode active material selected from the group consisting of a metal, a metal oxide and a mixed metal oxide, a metal sulfide and combinations thereof, electrically associated with a second cathode current collector; and iii) the electrolyte solution operatively associated with the second anode means and the second cathode means;

wherein the first cell is dischargeable independent of the second cell to provide separate and independent sources of electrical energy.

28. The electrochemical battery of claim 27 wherein the first electrochemical cell comprises the first cathode means having the first anode means disposed adjacent to at least one side of the cathode means, and wherein the second electrochemical cell comprises the second anode means and the second cathode means wound together in a jellyroll configuration.

29. The electrochemical battery of claim 28 wherein the first electrochemical cell comprises the first anode means disposed adjacent to opposite sides of the first cathode means at an intermediate position, between the first anode means.

30. The electrochemical battery of claim 28 wherein the first and second anode current collectors are electrically connected to the casing means to provide a case-negative configuration for the first and second cells.

31. The electrochemical battery of claim 28 wherein either of the first and second anode current collectors is electrically connected to the casing means to provide a case-negative configuration for the corresponding first and second electrochemical cells and the other of the first and second anode current collectors is connected to an anode terminal means electronically insulated from the casing means.

32. The electrochemical battery of claim 28 wherein both the first and second anode current collectors are electrically connected to respective anode terminal means electrically insulated from the casing means.

33. The electrochemical battery of claim 28 wherein the anode is comprised of lithium.

34. The electrochemical battery of claim 28 wherein the electrolyte solution operatively associated with both the first and second electrochemical cells comprises an inorganic salt having the general formula $MM'F_6$ dissolved in a nonaqueous solvent wherein M is an alkali metal similar to the alkali metal comprising at least one of the anode means and M' is an element selected from the group consisting of phosphorous, arsenic and antimony.

35. The electrochemical battery of claim 34 wherein the alkali metal of both the first and second anode means comprises lithium and the inorganic salt comprising the electrolyte solution is lithium hexafluorophosphate.

36. In combination with an implantable medical device requiring electrical power for a monitoring function and a device operating function, a battery comprising:
   a) a medium rate constant discharge or constant drain cell for providing low level currents for the monitoring function;
   b) a high rate pulse discharge cell for providing high level current for the operating function; and
   c) a single casing means containing both cells.

37. The combination of claim 36 wherein the casing has a prismatic shape.

38. A method of providing an electrochemical battery capable of simultaneous and independent discharge at both a substantially constant discharge rate and under a current pulse discharge application, which comprises:
   a) providing a casing means of electrically conductive material;
   b) housing a first electrochemical cell within the casing means comprising the steps of:
      i) providing a first anode means comprising alkali metal and electrically associating the alkali metal with a first anode current collector;
      ii) providing a first cathode means of cathode active material and electrically associating the first cathode active material with a first cathode current collector; and
      iii) activating the first electrochemical cell with an electrolyte solution operatively associated with the first anode means and the first cathode means; and
   c) housing a second electrochemical cell within the casing means comprising the step of:
      i) providing a second anode means comprising alkali metal and electrically associating the alkali metal with a second anode current collector;
      ii) providing a second cathode means of cathode active material and electrically associating the second cathode active material with a second cathode current collector; and
      iii) activating the second electrochemical cell with the electrolyte solution operatively associated with the second anode means and the second cathode. means.

39. The method of claim 38 including providing the first electrochemical cell to be dischargeable under a substantially constant discharge rate and providing the second electrochemical cell to be dischargeable under a current pulse discharge application.

40. The method of claim 38 including electrically connecting the first and second anode current collectors to the casing means to provide a case-negative configuration for the first and second cells.

41. The method of claim 38 including electrically connecting either of the first and second anode current collectors to the casing means to provide a case-negative configuration for the corresponding first and second electrochemical cell and connecting the other of the first and second anode current collectors to an anode terminal means electrically insulated from the casing means.

42. The method of claim 41 including electrically connecting both the first and second cathode current collectors to respective cathode terminal means electrically insulated from the casing means.

43. The method of claim 38 including electrically connecting both the first and second anode current collectors connected to respective anode terminal means electrically insulated from the casing means.

44. The method of claim 43 including electrically connecting both the first and second cathode current collectors to respective cathode terminal means electrically insulated from the casing means.

45. The method of claim 38 including providing the anode comprised of lithium.

46. The method of claim 38 including providing the electrolyte solution operatively associated with both the first and second electrochemical cells comprising an inorganic salt having the general formula $MM'F_6$ dissolved in a nonaqueous solvent, wherein M is an alkali metal similar to the alkali metal comprising at least one of the anode means and M' is an element selected from the group consisting of phosphorous, arsenic and antimony.

47. The method of claim 46 including providing the alkali metal of both the first and second anode means comprising lithium and providing lithium hexafluorophosphate as the inorganic salt comprising the electrolyte solution.

48. The method of claim 46 including providing the nonaqueous solvent comprising an organic solvent selected from the group consisting of tetrahydrofuran, propylene carbonate, methyl acetate, acetonitrile, dimethyl sulfoxide, dimethyl formamide, dimethyl acetamide, ethylene carbonate, diglyme, triglyme, tetraglyme, 1,2-dimethoxyethane and mixtures thereof.

49. The method of claim 38 including selecting the cathode active material of both the first and second cathode means from the group consisting of silver vanadium oxide, copper silver vanadium oxide, manganese dioxide, cobalt oxide, nickel oxide, copper oxide, titanium disulfide, copper sulfide, iron sulfide, iron disulfide copper vanadium oxide, carbon and fluorinated carbon and mixtures thereof.

* * * * *